(12) United States Patent
Millard et al.

(10) Patent No.: US 9,381,002 B2
(45) Date of Patent: Jul. 5, 2016

(54) DEVICE AND METHOD FOR CONDUCTING A PAP SMEAR TEST

(71) Applicants: Matthew D. Millard, La Jolla, CA (US); Imran Jawaid, Hollywood, CA (US); Winston L Alexis, Plantation, FL (US)

(72) Inventors: Matthew D. Millard, La Jolla, CA (US); Imran Jawaid, Hollywood, CA (US); Winston L Alexis, Plantation, FL (US)

(*) Notice: Subject to any disclaimer, the term of this patent is extended or adjusted under 35 U.S.C. 154(b) by 115 days.

(21) Appl. No.: 14/145,764

(22) Filed: Dec. 31, 2013

(65) Prior Publication Data

US 2015/0182205 A1    Jul. 2, 2015

(51) Int. Cl.
| | |
|---|---|
| *A61B 5/05* | (2006.01) |
| *A61B 10/04* | (2006.01) |
| *A61B 1/018* | (2006.01) |
| *A61F 6/04* | (2006.01) |
| *A61B 1/00* | (2006.01) |
| *A61B 1/303* | (2006.01) |
| *A61B 1/05* | (2006.01) |
| *A61B 1/06* | (2006.01) |
| *A61B 10/02* | (2006.01) |

(52) U.S. Cl.
CPC .............. *A61B 10/04* (2013.01); *A61B 1/00142* (2013.01); *A61B 1/018* (2013.01); *A61B 1/05* (2013.01); *A61B 1/0684* (2013.01); *A61B 1/303* (2013.01); *A61F 6/04* (2013.01); *A61B 2010/0216* (2013.01); *A61B 2034/2057* (2016.02); *A61B 2090/373* (2016.02)

(58) Field of Classification Search
CPC .............. A61B 10/04; A61B 19/5244; A61B 1/00142; A61B 1/018; A61B 1/05; A61B 1/0684; A61B 1/303; A61B 2010/0216; A61B 2019/5231; A61B 2019/5257
See application file for complete search history.

(56) References Cited

U.S. PATENT DOCUMENTS

| | | | | |
|---|---|---|---|---|
| 2006/0052662 | A1* | 3/2006 | Kress | A61B 1/0008 600/123 |
| 2007/0213590 | A1* | 9/2007 | Squicciarini | A61B 1/00087 600/172 |
| 2012/0232408 | A1* | 9/2012 | Weller-Brophy | A61B 1/00165 600/478 |
| 2013/0267870 | A1* | 10/2013 | Lonky | A61B 10/02 600/569 |

* cited by examiner

*Primary Examiner* — Mark Remaly
(74) *Attorney, Agent, or Firm* — John R. Ross; John R. Ross, III

(57) ABSTRACT

A protective guide for protecting a cell extraction device during a Pap smear. A camera protective cover encloses a camera and a light emitting device. A thin, flexible transparent sheath encloses the camera cover. A cell extraction device cover encloses the cell extraction device. The location of the cervix is determined by utilizing the camera. The cell extraction device is pushed outward from the cell extraction device cover so that said cell extraction device head contacts the cervix and removes cells from the cervix. The cell extraction device is pulled back into the cell extraction device cover after the cells have been removed from the cervix. In a preferred embodiment the camera and light emitting device is an endoscope and the camera cover is an endoscope cover.

10 Claims, 6 Drawing Sheets

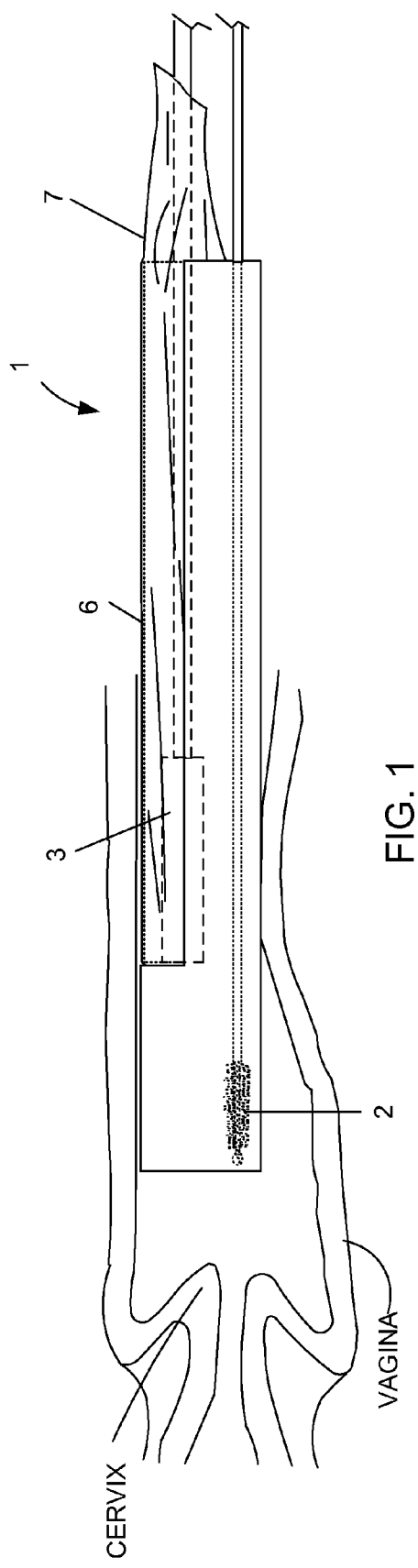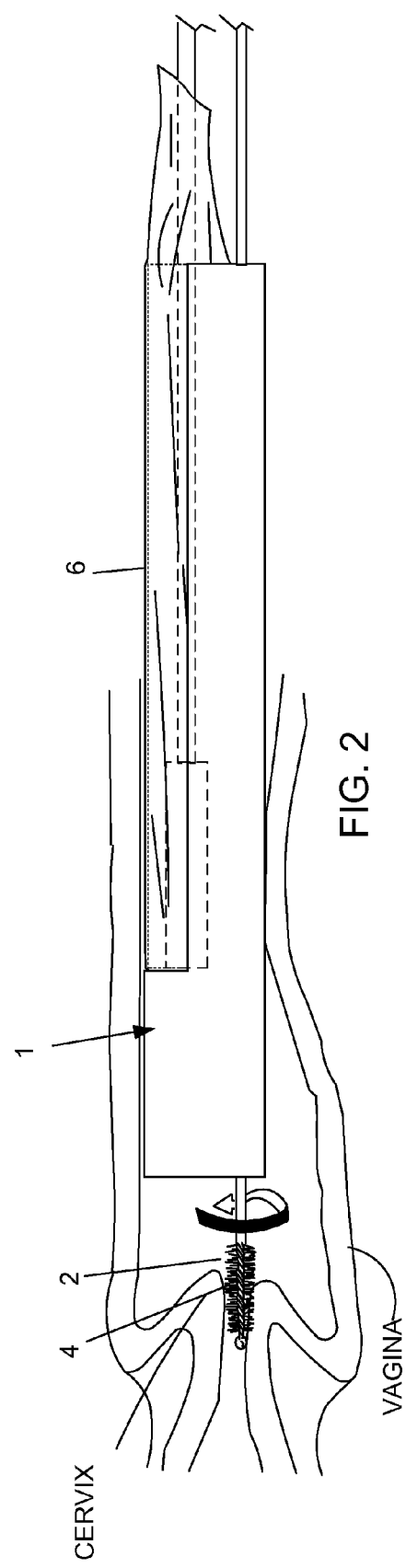

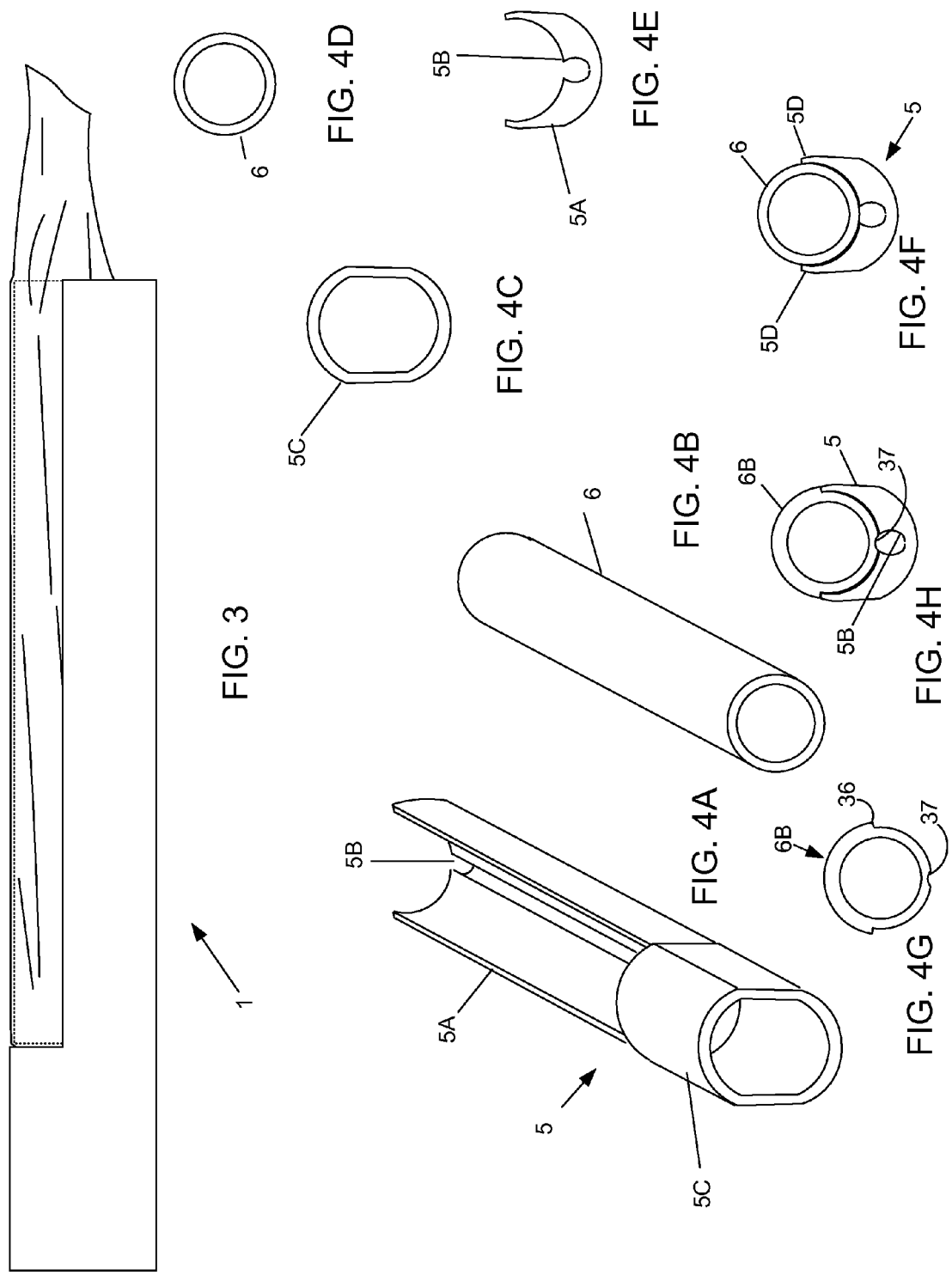

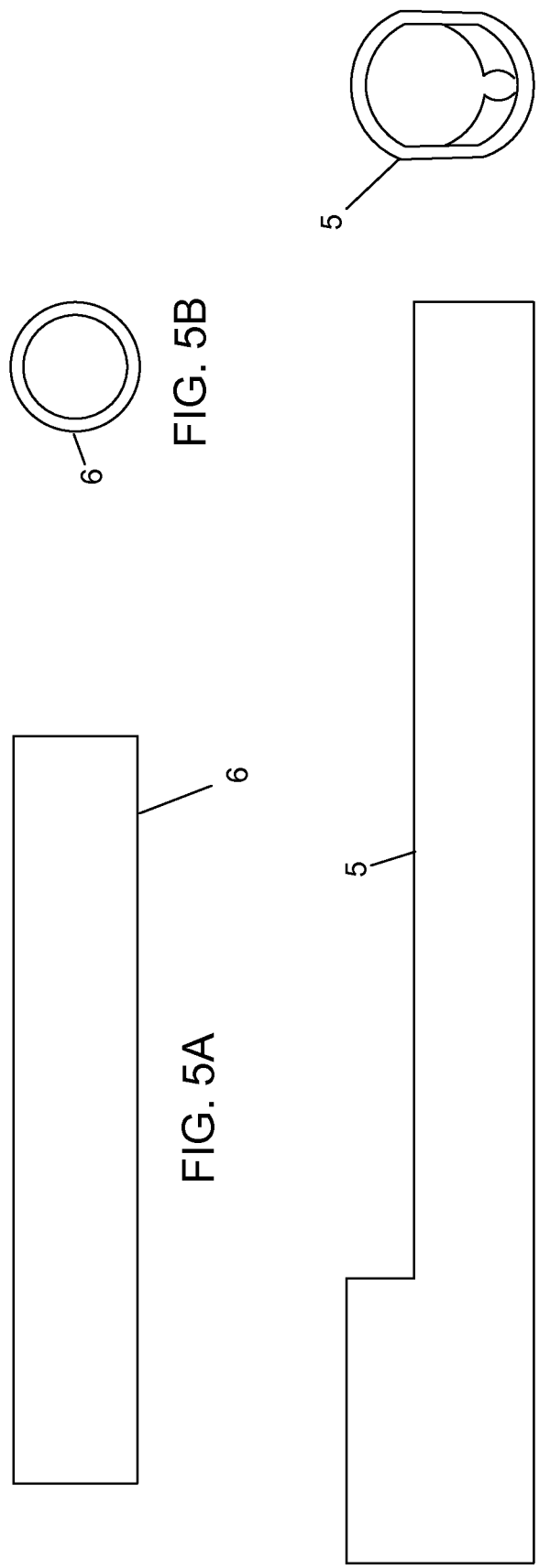

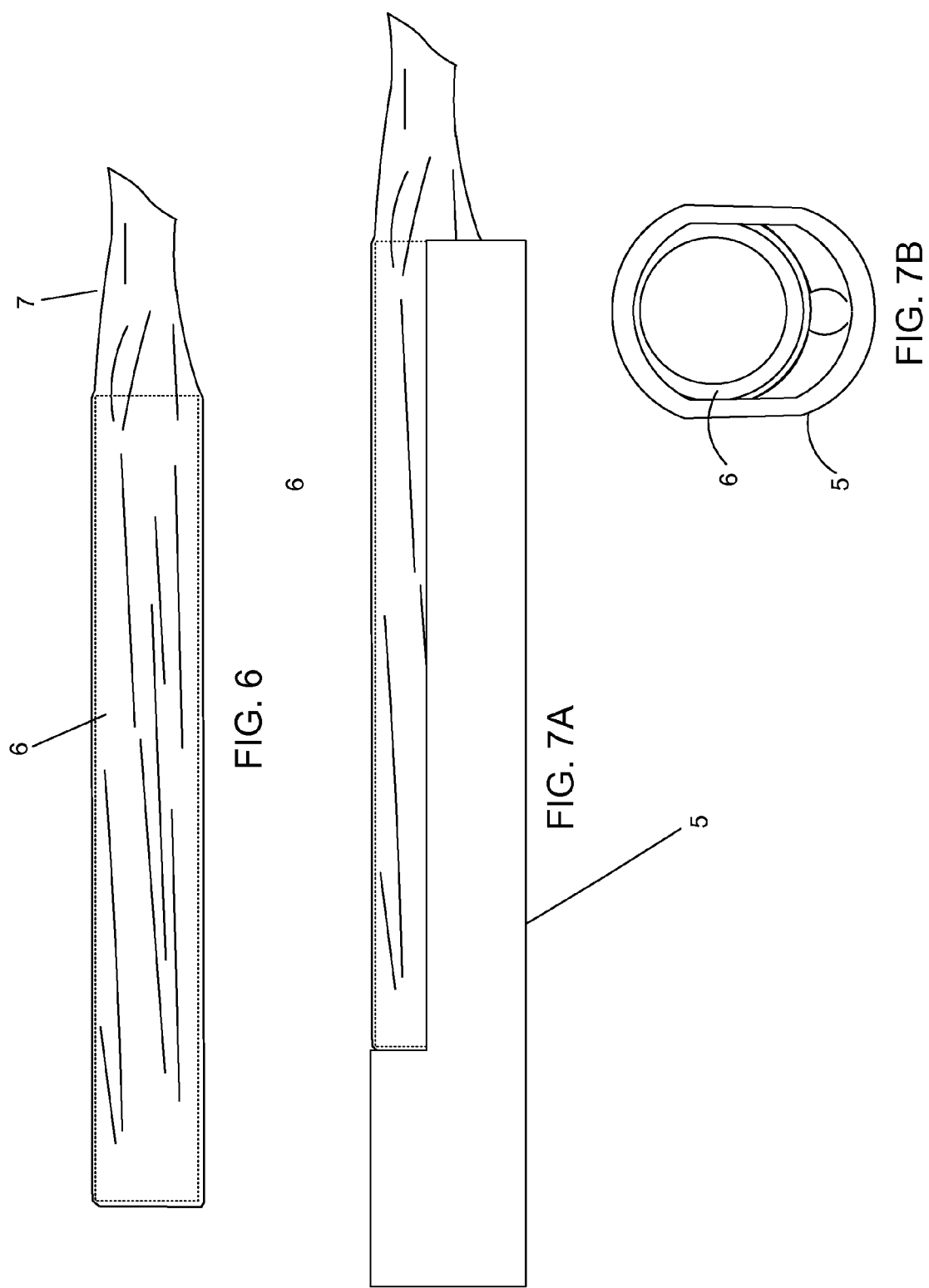

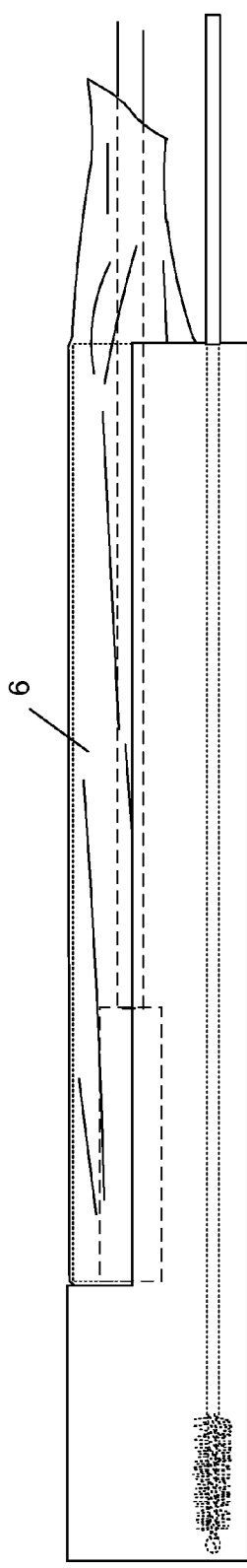
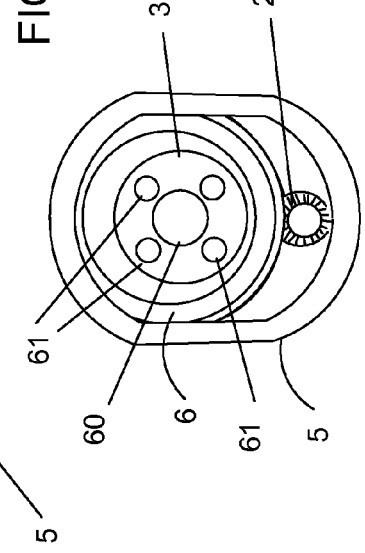
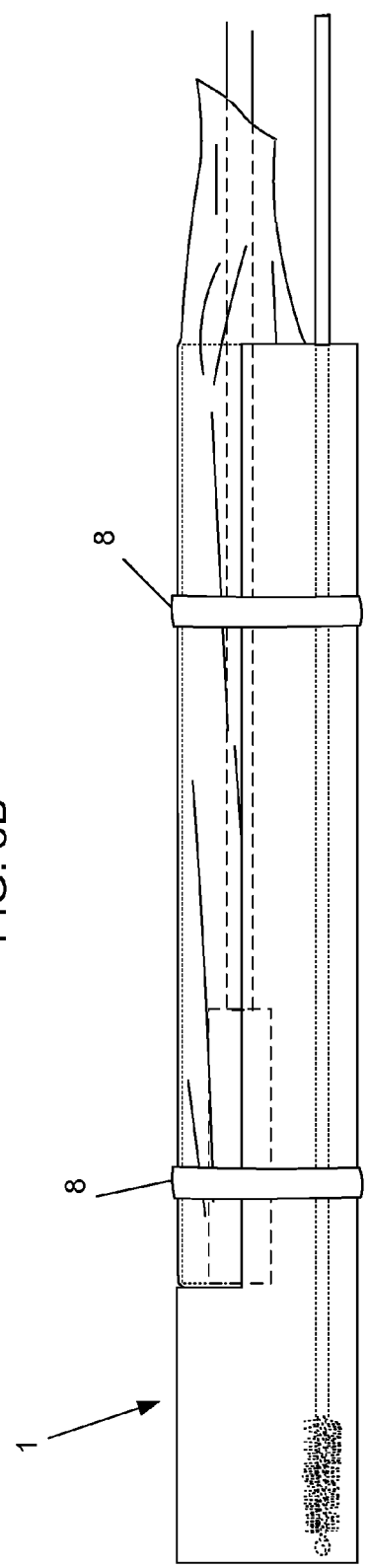
FIG. 8A
FIG. 8B
FIG. 9

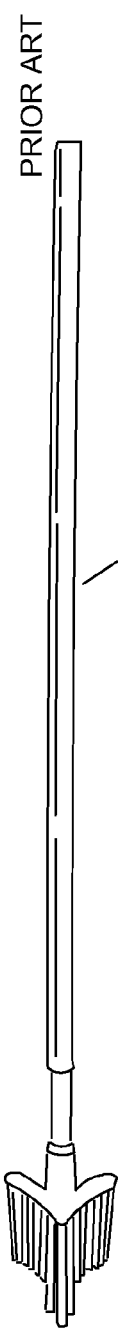
FIG. 10 PRIOR ART
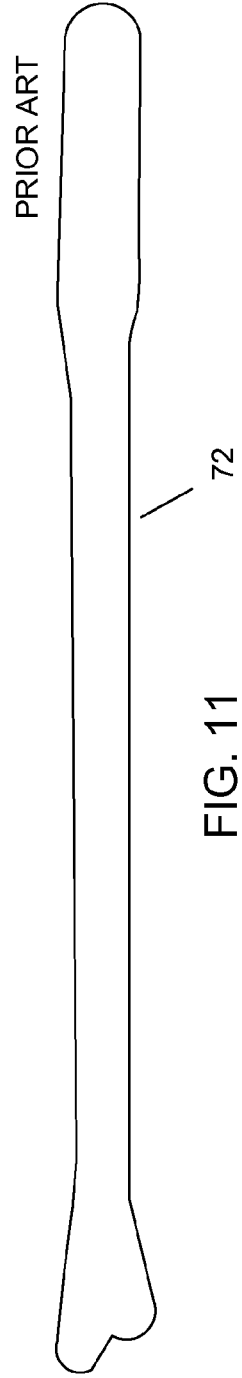
FIG. 11 PRIOR ART
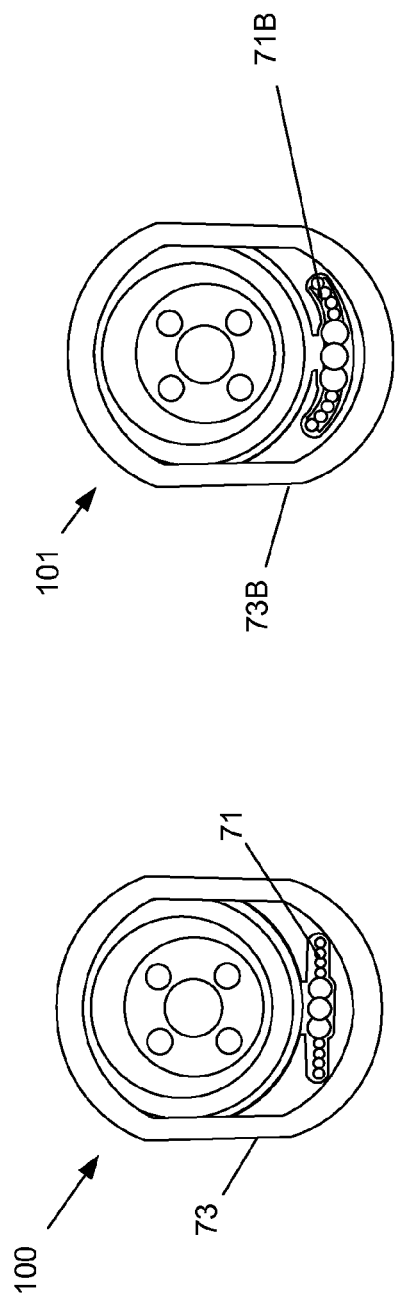
FIG. 12
FIG. 13

DEVICE AND METHOD FOR CONDUCTING A PAP SMEAR TEST

The present invention relates to medical devices and procedures, and in particular, to medical devices and procedures for conducting a Pap smear test.

BACKGROUND OF THE INVENTION

The Papanicolaou test (also called Pap smear, Pap test, cervical smear, or smear test) is a screening test used to detect potentially pre-cancerous and cancerous processes in the endocervical canal (transformation zone) of the female reproductive system.

A Pap smear is accomplished by usage of a cell extraction device such as a Pap smear spatula and Pap smear brush or alternatively by utilization of a Pap smear broom. In either case, the medical practitioner begins by inserting a speculum into the woman's vagina, which spreads the vagina open and allows access to the cervix. If using the spatula and brush, the medical practitioner then collects a sample of cells from the outer opening of the cervix by scraping it with the spatula. Then, an endocervical brush is rotated in the central opening of the cervix. Alternatively the medical practitioner may opt to use a plastic-fronded broom (Pap smear broom) in place of the spatula and brush. The cells are removed from the patient and are placed on a glass slide that is sent to a laboratory to be checked for abnormalities.

Speculum Problems

As stated above, the prior art method of conducting a Pap smear involves the use of a speculum to spread open the vagina. The utilization of the speculum can be extremely uncomfortable and painful to many women as the vagina is spread apart. Some women have even described the speculum as agonizing. The fear and apprehension associated with the speculum has unfortunately caused many women to delay the Pap smear test or, in some cases, to even avoid it entirely. This is unacceptable because it can allow preventable cancer to remain undiagnosed.

Endoscopes

Endoscopes are well known. The endoscope is a medical instrument for viewing the interior of the body and is used for diagnostic examinations and surgical procedures. The endoscope typically includes a USB endoscope camera, light emitting diodes (usually 4 LEDs) and a USB connection. The wide spread use of endoscopes can be attributed to their ease of use, in particular, how simple and inexpensive it is to connect the endoscope camera to a large screen, typically by a USB connection or a video cable. Additionally, LED's illuminate surfaces or spaces that would otherwise need to be surgically opened or enlarged to viewing width.

What is needed is a better device and method for conducting a Pap smear.

SUMMARY OF THE INVENTION

The present invention provides a protective guide for protecting a cell extraction device during a Pap smear. A camera protective cover encloses a camera and a light emitting device. A thin, flexible transparent sheath encloses the camera cover. A cell extraction device cover encloses the cell extraction device. The location of the cervix is determined by utilizing the camera. The cell extraction device is pushed outward from the cell extraction device cover so that said cell extraction device head contacts the cervix and removes cells from the cervix. The cell extraction device is pulled back into the cell extraction device cover after the cells have been removed from the cervix. In a preferred embodiment the camera and light emitting device is an endoscope and the camera cover is an endoscope cover.

BRIEF DESCRIPTION OF THE DRAWINGS

FIGS. 1 and 2 show the utilization of a preferred embodiment of the present invention.

FIG. 3 shows a side view of a preferred protective guide.

FIG. 4A-4H show views of a preferred brush cover and a preferred endoscope cover FIGS. 5A-8B show the utilization of a preferred embodiment of the present invention.

FIG. 9 shows another preferred embodiment of the present invention.

FIG. 10 shows a prior art Pap smear broom.

FIG. 11 shows a prior art Pap smear spatula.

FIG. 12 shows another preferred embodiment of the present invention.

FIG. 13 shows another preferred embodiment of the present invention.

DETAILED DESCRIPTION OF THE PREFERRED EMBODIMENTS

Protective guide 1 (FIG. 1) allows for a more comfortable, more efficient Pap smear in that a Pap smear can now be conducted without the utilization of a speculum. The patient no longer has to experience the fear, pain and apprehension commonly associated with a Pap smear. Protective guide 1 is very practical and low cost. It allows for very efficient and comfortable Pap smears.

FIGS. 1 and 2 show preferred Pap smear brush 2 and endoscope 3 protected by protective guide 1. Protective guide 1 is inserted into the vagina of a patient. Pap smear brush 2 is contained within protective guide 1. Endoscope 3 is enclosed within endoscope cover 6 of protective guide 1. Thin, flexible transparent latex cover 7 is wrapped around endoscope cover 5. In one preferred embodiment cover 7 is a condom.

In FIG. 1, the medical examiner has located the cervix by utilization of endoscope 3. In FIG. 2, the medical examiner has pushed Pap smear brush 2 outward so that brush head 4 is in contact with the cervix and surrounding tissue. The medical examiner is able to remove cells from the cervix for examination as shown. After the medical examiner has removed the cells from the cervix, he will retract the Pap smear brush back inside protective guide 1 so that it is in the position shown in FIG. 1. Protective guide 1 can then be withdrawn from the vagina.

Preferred Protective Guide

FIG. 3 shows a side view of a preferred protective guide 1. FIG. 4B shows a perspective view of endoscope cover 6 and FIG. 4A shows a perspective view of brush cover 5. Endoscope cover 6 is hollow and tubular. Brush cover 5 includes attachment section 5A, brush channel 5B, and front compartment 5C (see also FIGS. 4C-4F). Brush cover 5 preferably includes upper rails 5D which function to allow a secure press-fit with endoscope cover 6.

Protective guide 1 is preferably plastic and is preferably fabricated utilizing an injection molding process for a smooth texture. Brush channel 5B provides a tunnel that extends through protective guide 1 to allow access and movement for the Pap smear brush 2. When the Pap smear brush 2 is fully inserted inside brush channel 2 of protective guide 1, the brush head will be contained within the brush channel and covered by brush cover 5 and endoscope cover 6.

Utilization of a Preferred Protective Guide

FIG. 5A shows a side view and FIG. 5B shows a front view of endoscope cover 6. FIG. 5C shows a side view and FIG. 5D shows a front view of brush cover 5.

In FIG. 6 the user has placed endoscope cover 6 inside thin, transparent latex cover 7. Latex cover 7 functions as a sheath and as a protective barrier. It covers and protects the endoscope and a portion of the endoscope cord as well as providing for a more comfortable insertion of protective guide 1 into the vagina. It also prevents germs and bacteria that may be present on the endoscope or that may be present on the endoscope cord from coming in contact with the patient. Latex cover 7 is transparent and allows for unobstructed viewing via the endoscope camera.

In FIGS. 7A and 7B the user has press fit endoscope cover 6 into brush cover 5 so that brush cover 5 is held in place by friction force.

In FIGS. 8A-8B the user has inserted endoscope 3 into endoscope cover 6 and he has inserted Pap smear brush 2 into brush cover 5. FIG. 8B shows a front view of endoscope 3 with camera 60 and light emitting diodes (LEDS) 61. Protective guide 1 is now ready for insertion into the patient's vagina.

FIG. 9 shows an optional embodiment in which bands 8 have been wrapped around protective guide 1. Bands 8 provide reinforcement to the press fit between endoscope cover 6 and brush cover 5.

In FIG. 1 protective guide 1 has been inserted into the patient's vagina. The image provided by endoscope 3 is providing the medical examiner with a good image of the cervix.

In FIG. 2, the medical examiner has pushed brush 2 outward so that broom head 10 is able to contact the cervix. The bristles of brush head 4 are inserted into the endocervical canal so that they are able to fully contact the ectocervix. The medical examiner preferably pushes gently, and rotates brush section 10 in a clockwise direction five times. After completion the medical examiner may retract brush head back into protective guide 1 and then remove protective guide 1 from the vagina.

OTHER EMBODIMENTS

Other embodiments of the present invention may also be utilized. For example, brush 2 may be replaced with Pap smear broom 71 (FIG. 10) or Pap smear spatula 72 (FIG. 11).

FIG. 12 shows protective guide 100 utilizing Pap smear broom 71 and broom cover 73.

FIG. 13 shows protective guide 101 utilizing Pap smear broom 71B and broom cover 73B. Pap smear broom 71B is contoured so that it follows the curvature of broom cover 73B. This allows for the head of broom 71B to made with greater surface area.

Also, FIGS. 4G and 4H show a preferred endoscope cover 6B. Endoscope cover 6B includes lip 36 and dimple 37. Lip 36 allows for a smoother fit when endoscope cover 6B is press fit onto brush cover 5. This increases comfort for the patient. Also dimple 37 corresponds with brush channel 5B of brush cover 5 for a better fit for Pap smear brush 2.

Although the above-preferred embodiments have been described with specificity, persons skilled in this art will recognize that many changes to the specific embodiments disclosed above could be made without departing from the spirit of the invention. For example, even though the above preferred embodiments referred to the utilization of an endoscope and an endoscope cover, it should be understood that other types of cameras could also be substituted and the LEDS from the endoscope could also be replaced with other types of light emitting devices. Also, endoscope cover 6 may also be referred to as a camera cover. Therefore, the attached claims and their legal equivalents should determine the scope of the invention.

What is claimed is:

1. A protective guide for protecting a cell extraction device during a Pap smear, comprising:
   A. a camera,
   B. a light emitting device,
   C. a camera cover covering said camera and light emitting device,
   D. a thin flexible transparent sheath covering said camera cover,
   E. a cell extraction device cover for covering said cell extraction device, and wherein the location of the cervix is determined by utilization of said camera, wherein said cell extraction device is pushed outward from said cell extraction device cover so that said cell extraction device head contacts the cervix and removes cells from the cervix, wherein said cell extraction device head is pulled back into said cell extraction device cover after said cells have been removed from the cervix.

2. The protective guide as in claim 1, wherein said camera and light emitting device is an endoscope and said camera cover is an endoscope cover.

3. The protective guide as in claim 1, wherein said thin flexible transparent sheath is a condom covering said camera cover.

4. The protective guide as in claim 2, wherein said thin, flexible transparent sheath covers said endoscope cover, said endoscope and an endoscope cord.

5. The protective guide as in claim 1, wherein said cell extraction device cover comprises a tunnel and wherein said cell extraction device is inserted into said tunnel.

6. The protective guide as in claim 1, wherein said camera cover and said cell extraction device cover are press fit together.

7. The protective guide as in claim 1, further comprising at least one elastic band for holding said camera cover and said cell extraction device cover together.

8. The protective guide as in claim 1, wherein said cell extraction device is a Pap smear brush.

9. The protective guide as in claim 1, wherein said cell extraction device is a Pap smear broom.

10. The protective guide as in claim 1, wherein said cell extraction device is Pap smear spatula.

* * * * *